US005463782A

United States Patent [19]
Carlson et al.

[11] Patent Number: 5,463,782
[45] Date of Patent: Nov. 7, 1995

[54] FOLDABLE STOOL SAMPLE COLLECTION DEVICE

[75] Inventors: Eric V. Carlson, 17170 Wall St., Lake Oswego, Oreg. 97034; Iraj Nikzi, Beaverton, Oreg.

[73] Assignee: Eric V. Carlson, Lake Oswego, Oreg.

[21] Appl. No.: 342,754

[22] Filed: Nov. 21, 1994

[51] Int. Cl.$^6$ .................................................. A47K 11/00
[52] U.S. Cl. ........................................................ 4/661
[58] Field of Search .......................... 4/315, 661, 144.1, 4/144.2; 128/749; 604/322, 326

[56] References Cited

U.S. PATENT DOCUMENTS

| | | |
|---|---|---|
| 2,840,826 | 7/1958 | Ebbesen et al. . |
| 3,588,921 | 6/1971 | Nagel . |
| 3,754,287 | 8/1973 | Taylor . |
| 3,775,777 | 12/1973 | Roberts, Jr. . |
| 4,101,279 | 7/1978 | Aslam . |
| 4,309,782 | 1/1982 | Paulin . |
| 4,445,235 | 5/1984 | Slover et al. . |
| 4,521,520 | 6/1985 | Jacke . |
| 4,720,880 | 1/1988 | Barreau . |
| 4,935,969 | 6/1990 | Farnsworth ............................ 4/661 X |
| 5,337,426 | 8/1994 | Matusewicz et al. ...................... 4/661 |
| 5,412,819 | 5/1995 | Matusewicz et al. ...................... 4/661 |

Primary Examiner—Charles E. Phillips
Attorney, Agent, or Firm—Chernoff, Vilhauer et al.

[57] ABSTRACT

A stool sample collection device including a sheet of preferably foldable material which has at least three extensions formed from the sheet which meet generally at an intersection, Attachment apparatus such as a removable adhesive is located at respective ends of the extensions distal from the intersection. A cupping section is formed from the sheet generally at the intersection of the extensions. The cupping section includes at least two webbing sections: a first webbing section formed generally between a first longitudinal extension and a central or support extension and a second webbing section formed generally between the central or support extension and a second longitudinal extension. The webbing sections would preferably include fold lines to add shape and rigidity to the cupping section. The device may be used by using the attachment apparatus to attach the device to a rim of a toilet bowl so that the cupping section depends into the toilet bowl.

16 Claims, 8 Drawing Sheets

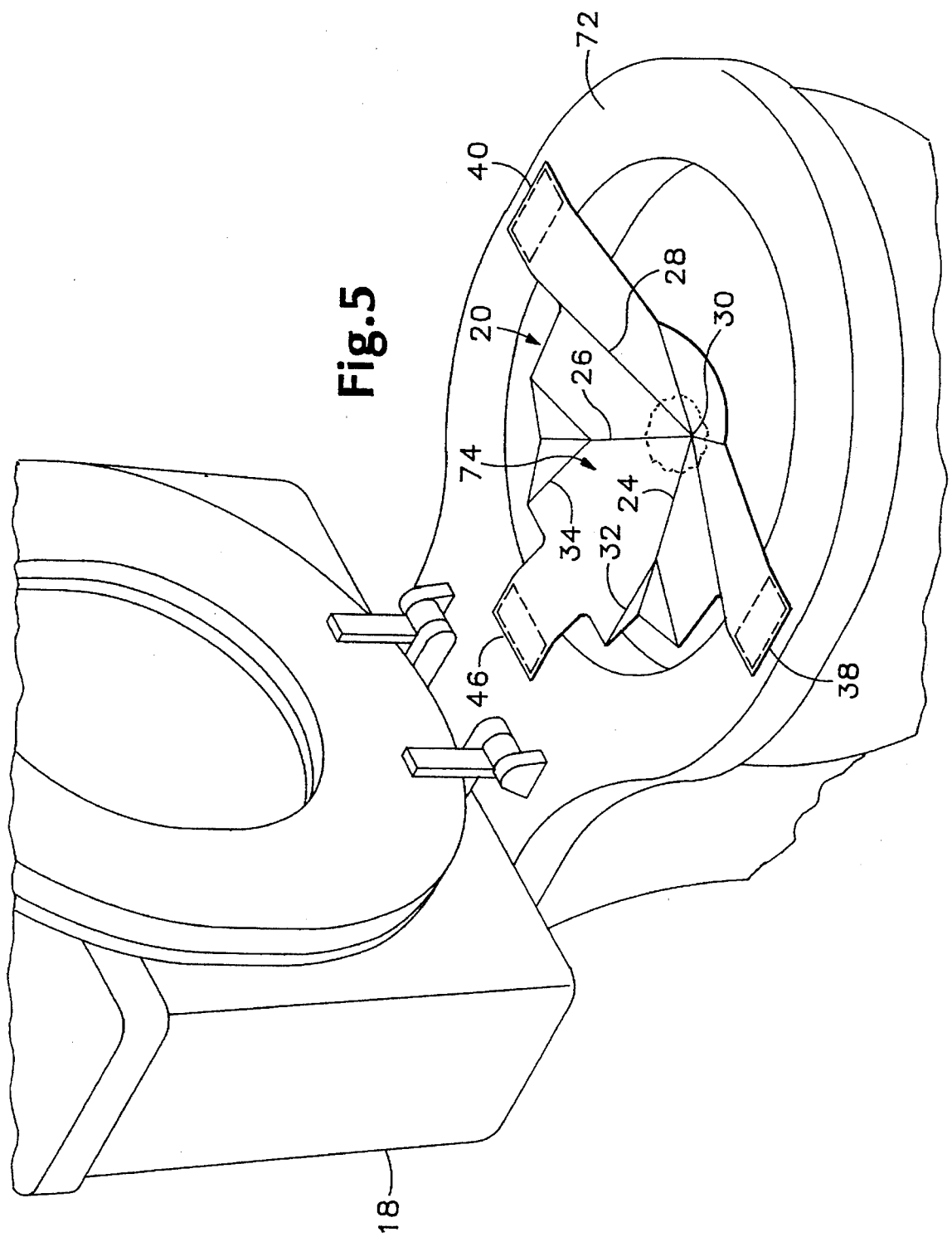

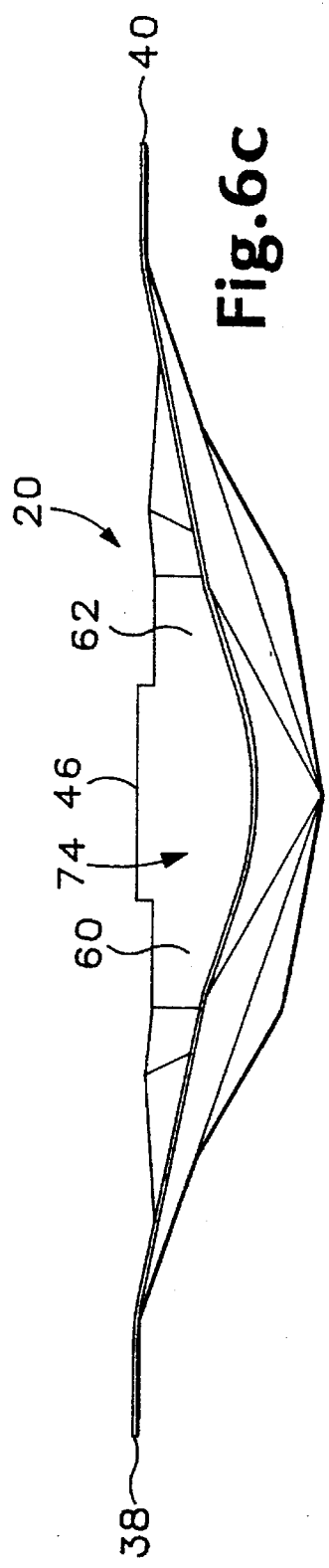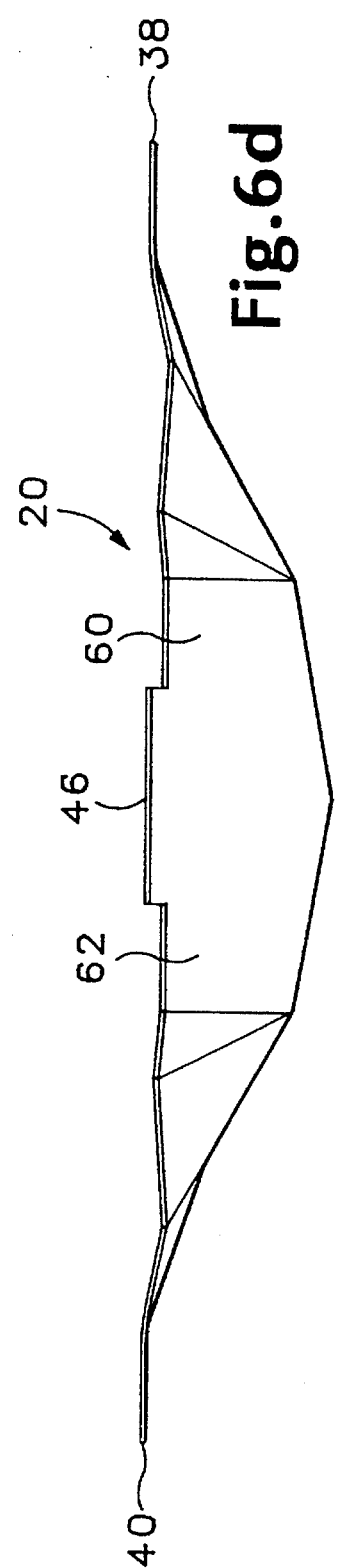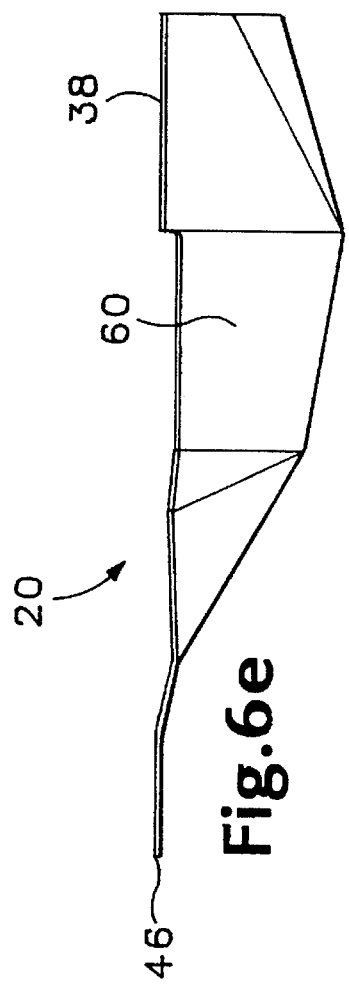

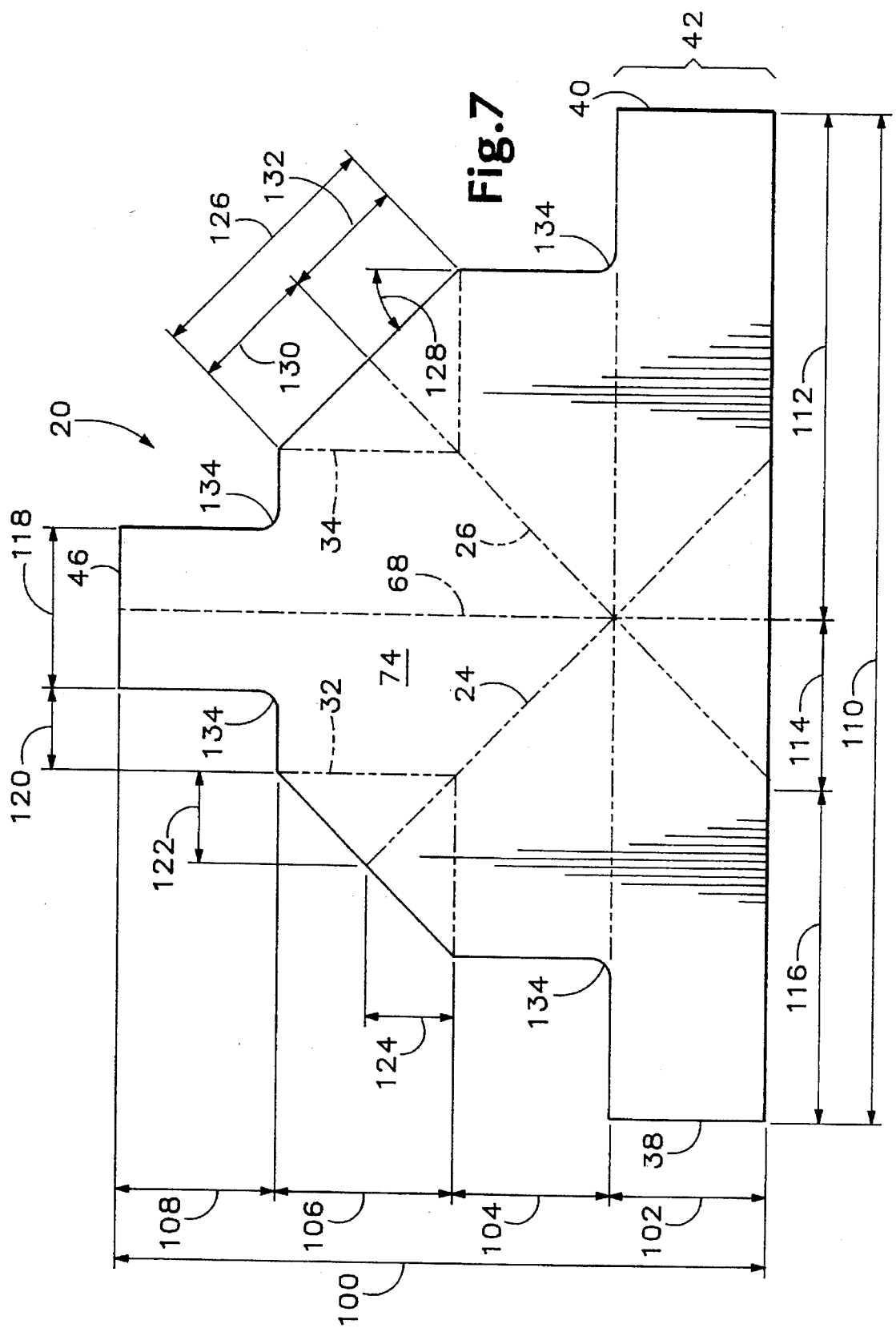

5,463,782

FOLDABLE STOOL SAMPLE COLLECTION DEVICE

BACKGROUND OF THE INVENTION

This invention relates to an apparatus for stool sample collection and particularly to a foldable, disposable stool sample collection device.

Because stool samples can often provide valuable information regarding the health of a patient, medical practitioners often require a patient to provide a stool sample for diagnostic and treatment purposes. Tests can be performed on the stool sample to indicate the presence of microorganisms such as parasites, bacteria, and viruses. Stool samples can also be examined for the presence of occult blood which can often be an indication of cancer. For these tests to be accurate, the stool sample should not be contaminated by urine or toilet water.

Methods for collecting stool samples often consist of having the patient provide the sample on a newspaper, in a cup, or on a piece of tissue. These methods, however, tend to be embarrassing, awkward, and distasteful.

Some devices specifically designed for the purpose of stool collection tend to be unnecessarily complicated in that they require the use of specially designed holders or support means. Other devices, because of the materials used or the construction of the device, tend to be expensive to produce. Still other devices are ineffective because they allow the mixing of urine or toilet water with the stool sample, are not sturdy enough to support the stool sample, or are not shaped in a manner designed to catch the stool and prevent it from escaping into the toilet bowl.

What is needed is an effective device which allows the patient to easily and comfortably collect a stool sample. Further, the device should be inexpensive to produce and require a minimum of assembly. Finally, the device should be designed for ease of shipment and storage.

SUMMARY OF THE INVENTION

The present invention is a stool sample collection device which allows a patient to defecate in a normal manner using a conventional flush toilet. Further, the invention enables the collection of the stool sample in such a manner that the specimen is not contaminated by urine or toilet water which may adversely affect the results of the tests or analysis performed on the specimen. The present invention is also lightweight and foldable which make it convenient for shipping and storage.

A stool sample collection device according to the present invention includes a sheet of material which is preferably foldable. The device preferably has at least three extensions formed from the sheet, the extensions meeting generally at an intersection. In the preferred embodiment, an attachment apparatus such as an adhesive tab would be located at respective ends of the extensions distal from the intersection. Preferably, a cupping section would be formed from the sheet generally at the intersection of the extensions. The cupping section would preferably include at least two webbing sections: a first webbing section formed generally between a first longitudinal-extension and a central or support extension and a second webbing section formed generally between the central or support extension and a second longitudinal extension. The webbing sections would preferably include fold lines to add shape and rigidity to the cupping section. The device would be used by using the attachment apparatus to attach the device to a rim of a toilet bowl so that the cupping section depends into the toilet bowl.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 5 is a perspective view of the invention installed in its operative position on the toilet bowl.

FIGS. 6a–6e are perspective views of the invention taken from the top, bottom, front, back, and side.

FIG. 7 is a top plan view of the preferred embodiment of the invention.

DETAILED DESCRIPTION OF THE PREFERRED EMBODIMENT

The figures show an exemplary embodiment of a stool sample collection device, indicated generally as 20, for collecting a stool sample in such a manner that a patient may defecate in a normal manner using a conventional flush toilet 18 and the sample will be deposited in the collection device 20 without the sample being contaminated-by urine or toilet water.

Figure 1:
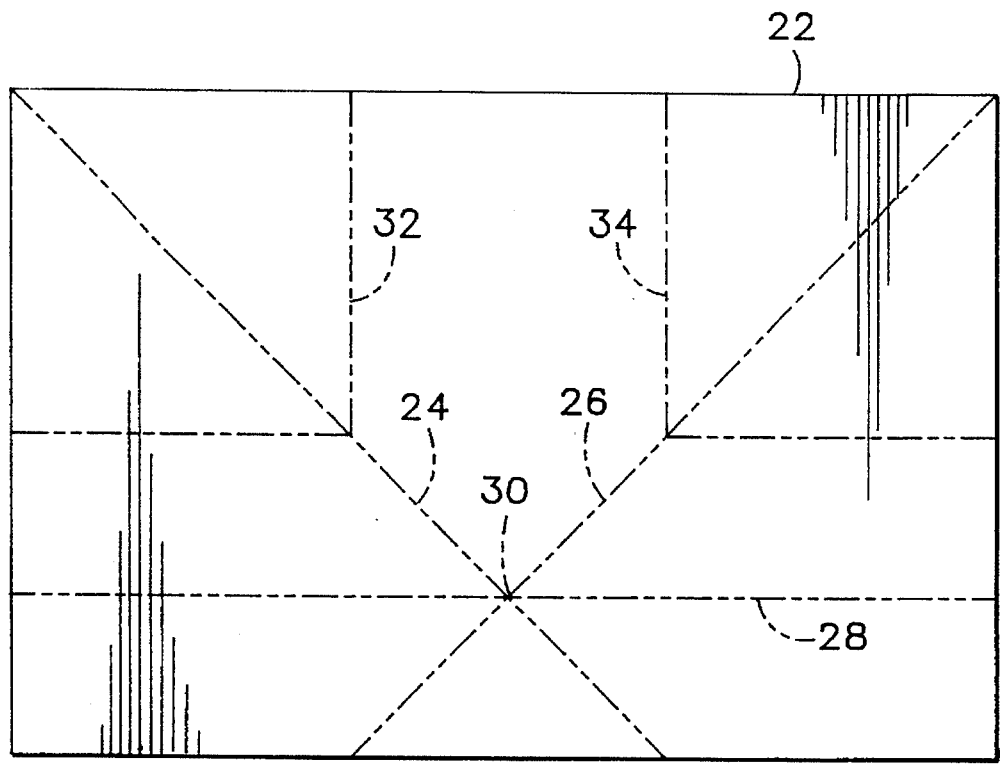
FIG. 1 is a top plan view of a sheet of material used to construct the invention having fold lines.
Figure 2:
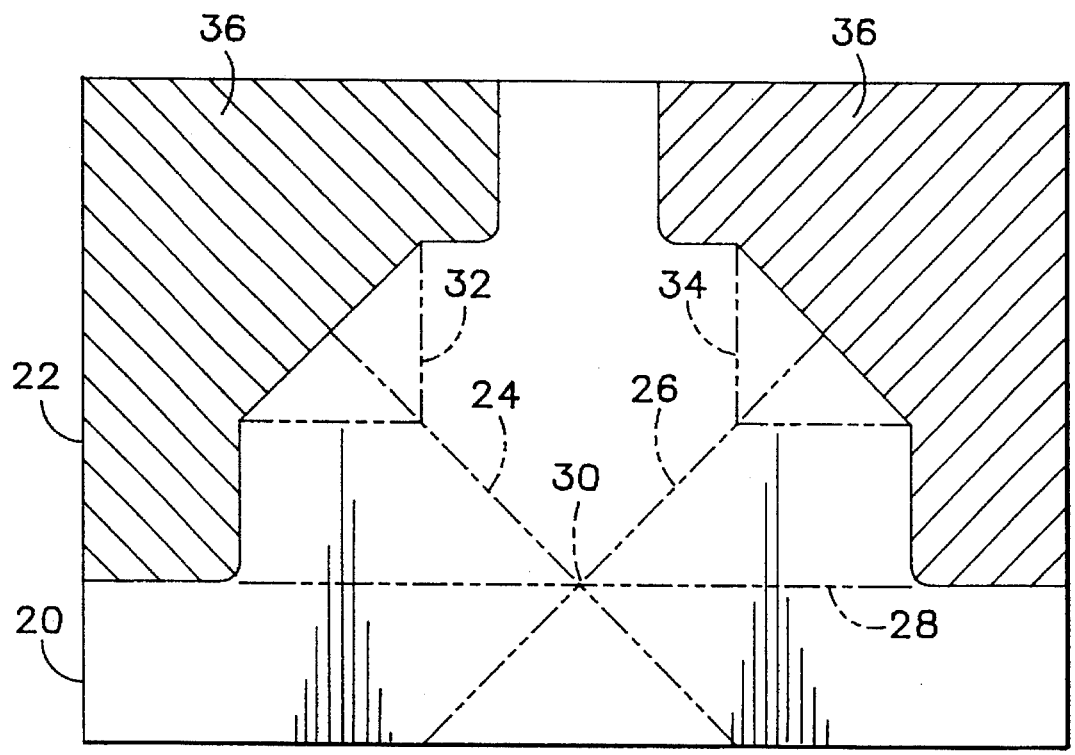
FIG. 2 is a top plan view of a die-cut sheet of the material of FIG. 1.

FIGS. 1 and 2 show the initial construction of the collection device 20. FIG. 1 shows a sheet of material 22 which preferably has five types of fold lines. The material used for the sheet 22 is preferably a light-weight, disposable material which can be folded or scored and has sufficient strength to support a stool sample. The material is also preferably biodegradable. Accordingly, appropriate materials would include, but are not limited to lightweight paper products such as tissue paper, fabrics, or plastics. The paper may also be appropriately treated with coatings to add strength such as a wax coating.

The first and second fold lines 24 and 26 of FIG. 1 are preferably diagonal fold lines which intersect in the bottom half of the sheet of material 22. The third fold line 28 is preferably a longitudinal fold line 28 generally intersecting at the intersection 30 of the first and second diagonal fold lines 24 and 26. The fourth fold line 32 is preferably a backward L-shaped fold 32 on the upper left corner of the sheet 22 which approximately forms a square with the upper left corner edges of the sheet 22. The fifth fold line 34 is preferably an L-shaped fold 34 on the upper right corner of the sheet 22 which approximately forms a square with the upper right corner edges of the sheet 22. Preferably, the fold lines (24, 26, 28, 32, and 34) on the left and right sides of the sheet 22 should be symmetrical about the transverse center line of the sheet. After folding, the sheet is cut to the desired shape.

FIG. 2 shows the approximate sections 36 of the sheet 22 which are removed or cut away to form the collection device 20. Preferably, the sheet 22 is die cut, however, other methods may be used.

Figure 3:
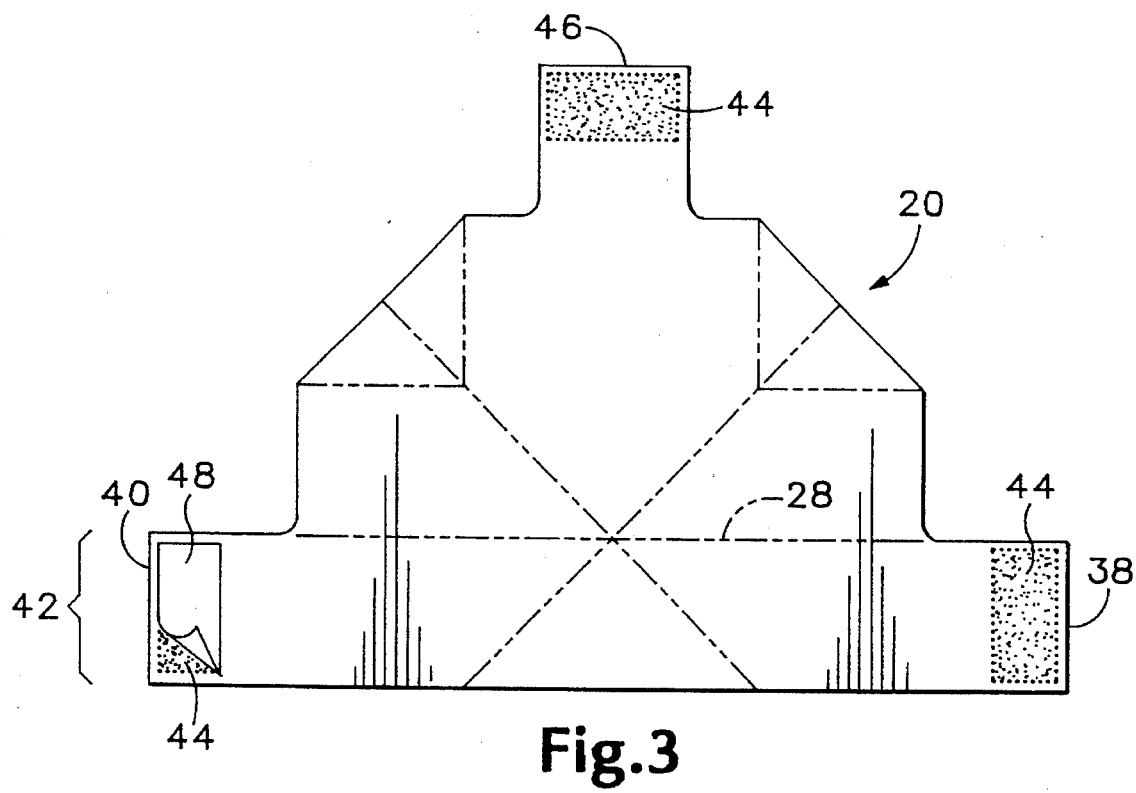
FIG. 3 is a bottom plan view showing the location of the adhesive on the invention.
Figure 4A:
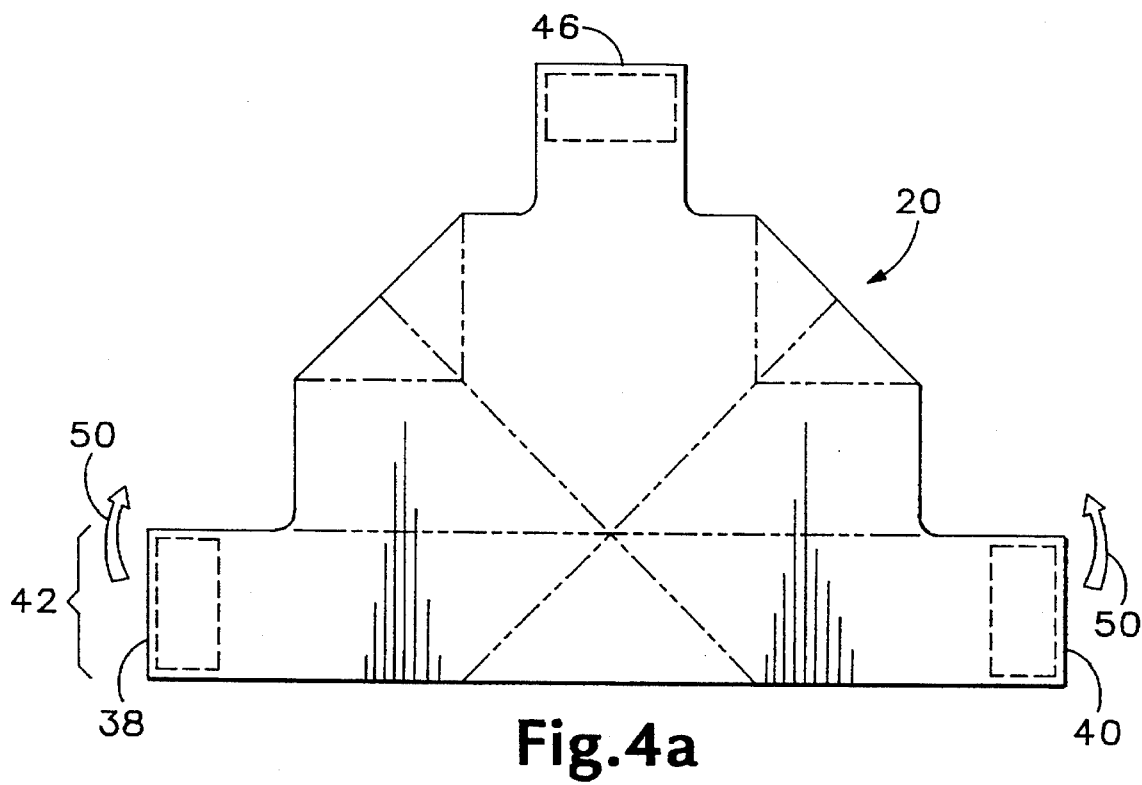
FIGS. 4a–4e are perspective views of the folding process of the invention.

FIG. 3 shows a bottom plan view of the collection device 20 and FIG. 4a shows a top plan view of the collection device 20. These views show the left and right longitudinal extensions 38 and 40 defined by and on opposite ends of a strip 42 of the sheet 22 that is formed between the lower edge of the sheet 22 and the longitudinal fold line 28. The longitudinal extensions 38 and 40 preferably have attachment apparatus 44 formed thereon and discussed below.

FIGS. 3 and 4a further show a support extension 46 formed from the sheet 22. The support extension 46 is preferably midway between and perpendicular to the longitudinal extensions 38 and 40. Similar to the longitudinal extensions 38 and 40, the support extension 46 also has attachment apparatus 44 formed thereon.

FIG. 3 shows the preferred location of the attachment apparatus 44 at the bottom side of the end sections of the extensions 38, 40, and 46. Preferably, the attachment apparatus 44 is a removable or lightly tacky adhesive such as the 3M adhesive used on POST-IT brand notes. This adhesive is also referred to as a clean stick adhesive because it may be secured to a surface and yet easily removed. The attachment apparatus 44 may be protected during shipping and storage by a removable protective covering such as a protection strip 48 of material which would be removed prior to the attachment apparatus being attached to a toilet 18 (shown in FIG. 5). An alternate method of protecting the preferred attachment apparatus 44 would include folding the respective extensions 38, 40, and 46 so that the attachment apparatus 44 attaches to the sheet of material 22 (shown in FIG. 4e). The respective extensions are unfolded so that the attachment apparatus 44 are removed from the sheet of material 22 so that the attachment apparatus 44 may be attached to a toilet 18 (shown in FIG. 5).

Figure 4B:
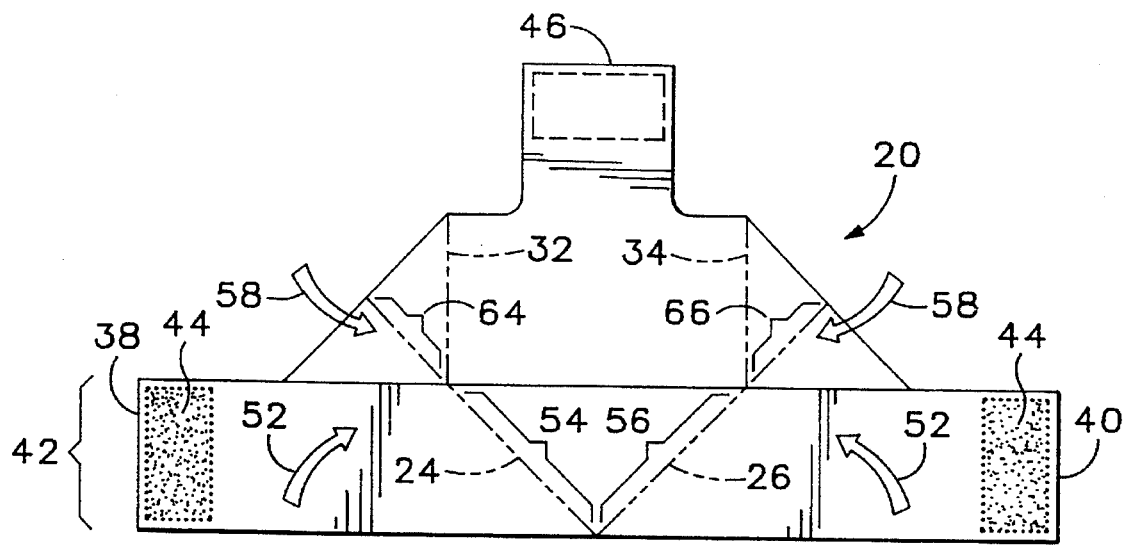

The preferred embodiment of the collection device 20 is foldable for easy shipment and storage. FIGS. 4a–4e are perspective views of the folding process. FIG. 4a shows the collection device 20 with arrows 50 indicating that strip 42 is to be folded upward along longitudinal fold line 28. FIG. 4b shows the collection device 20 after the strip 42 has been folded upward.

Figure 4C:
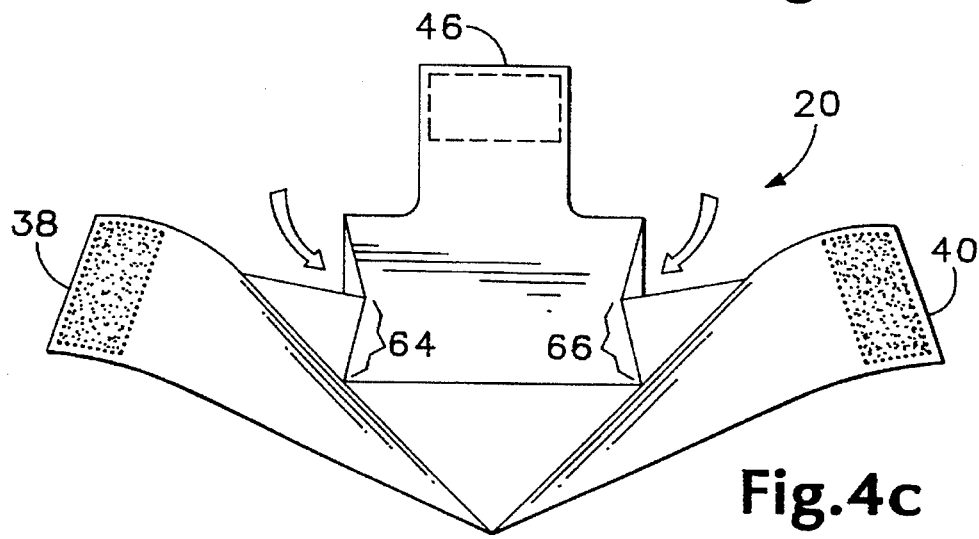
Figure 6A:
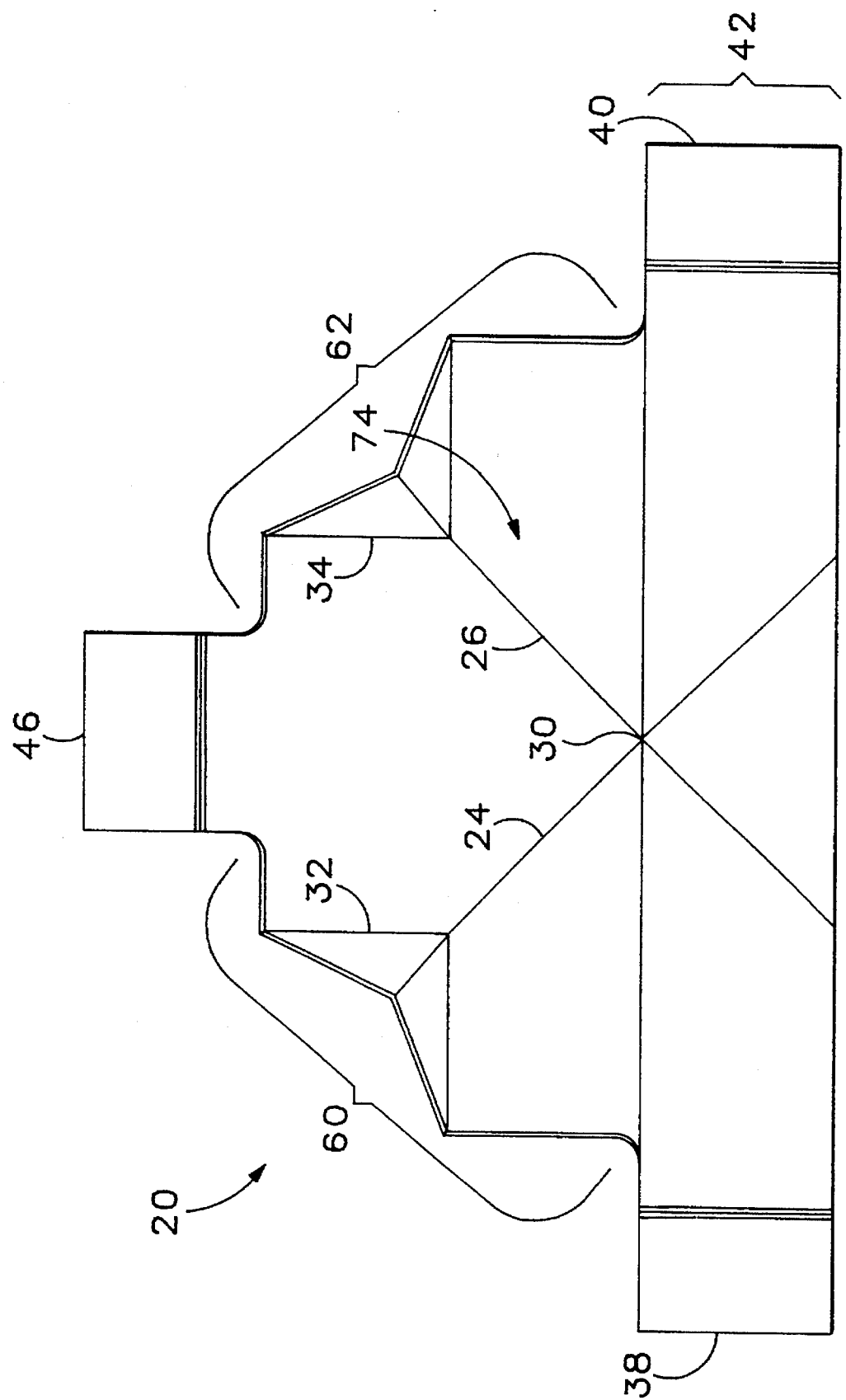
Figure 6B:
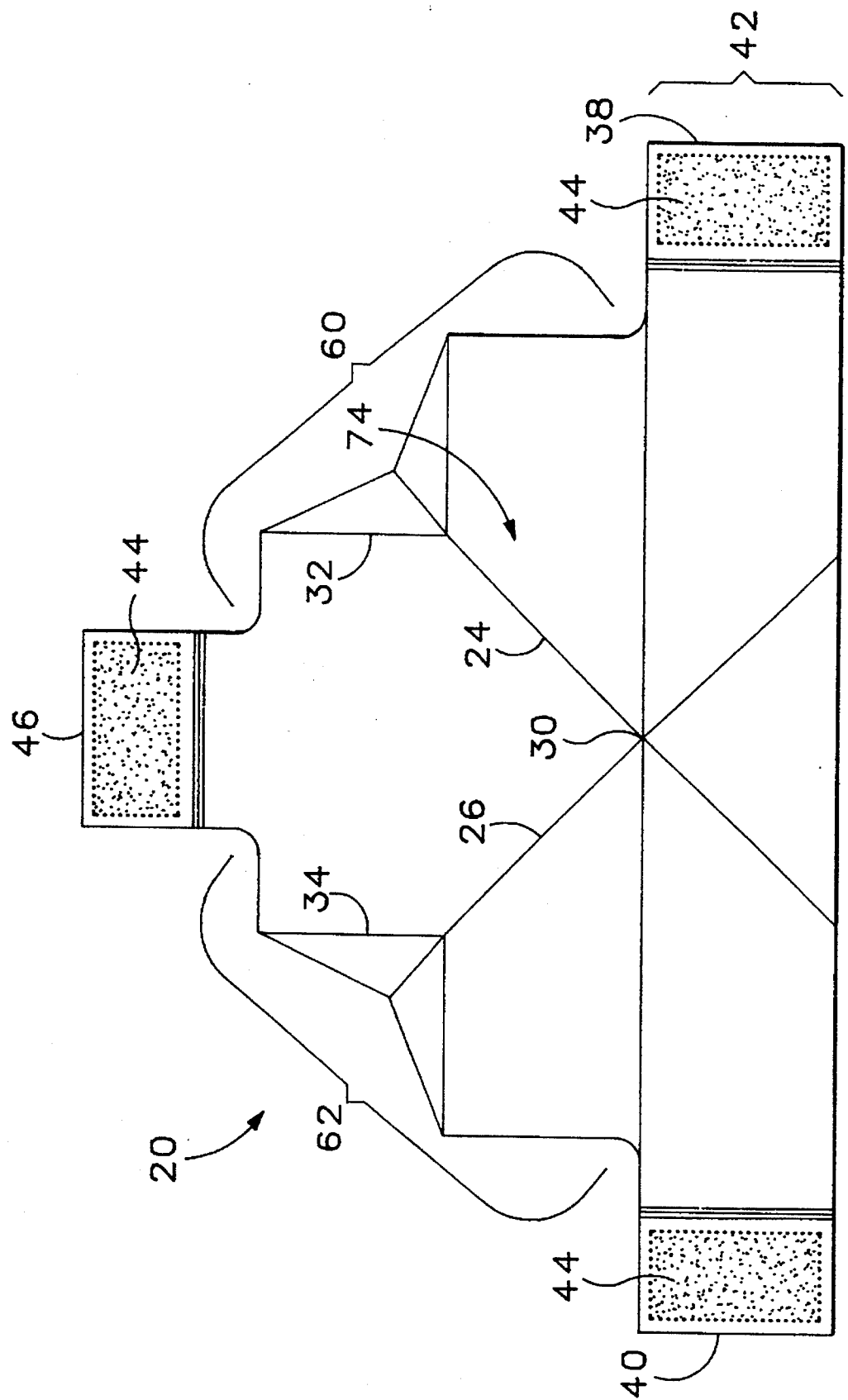

FIG. 4b also shows arrows 52 indicating that extensions 38 and 40 are to be folded upward along the double layered or folded sections 54 and 56 of diagonal fold lines 24 and 26, respectively. Arrows 58 indicate that a portion of webbing sections 60 and 62 (as shown in FIGS. 6a and 6b discussed below) defined by the fourth fold line 32 (backward L-shaped fold) and fifth fold line 34 (L-shaped fold) folds inward along fold lines 32 and 34 which are bisected by the sections 64 and 66 of the fold lines 24 and 26, respectively. Accordingly, in the preferred embodiment of the invention, the sections 64 and 66 of the fold lines 24 and 26 are angled generally toward the center line 68 of the object (FIG. 7). FIG. 4c shows the collection device 20 in the process of being folded along in the directions indicated by arrows 52 and 58.

Figures 4D, 4E:
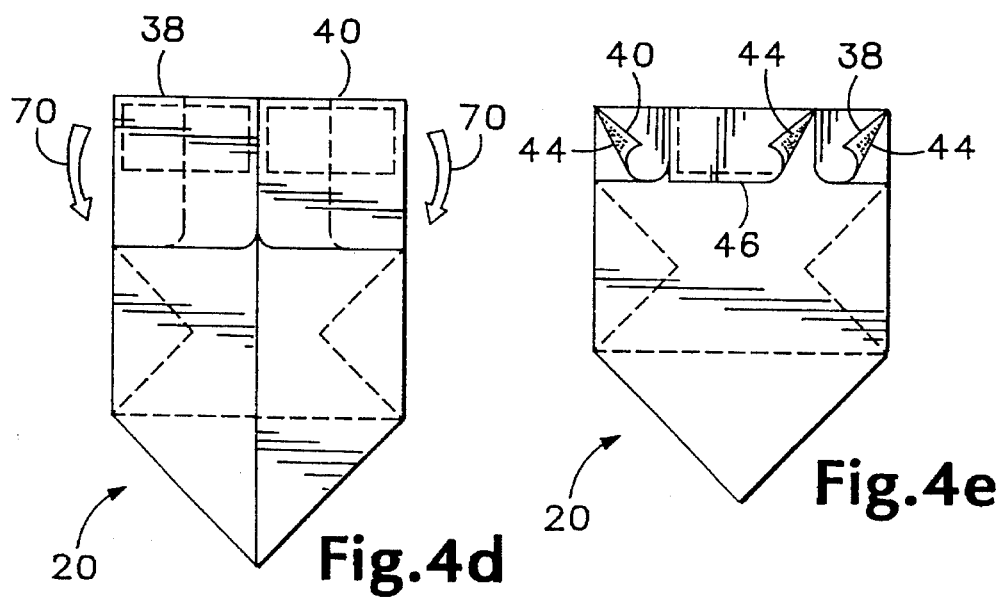

FIG. 4d shows the collection device 20 in a preferred embodiment of a final folded state. If this embodiment is to be the final folded state, the attachment apparatus 44, if it is adhesive, would preferably be protected by a removable protective covering 48. An alternative final folded state is indicated by arrows 70 which indicate that the attachment apparatus 44 may be folded to attach to the sheet of material 22. FIG. 4e shows this alternative folded state.

FIG. 5 shows the collection device 20 installed in its operative position on the toilet bowl 18. To install the collection device, the attachment apparatus 44 on the extensions 38, 40, and 46 are removably attached to a rim 72 of the toilet 18 so that the longitudinal extensions 38 and 40 are attached to the sides of the rim 72 and the support extension 46 is attached to the back of the rim 72.

When installed as shown in FIG. 5, a cupping section 74 is formed by the sheet of material 22 with the lowest point generally at the intersection 30. The cupping section 74 is generally formed by the first and second diagonal fold lines 24 and 26 and the longitudinal fold line 28. The additional fold lines 32 and 34 also help to form the cupping section 74 and further add extra rigidity to the cupping section 74 as they bend to form the raised back portion of the cupping section 74. Further, the cupping section 74 is located generally between the left and right longitudinal extensions 38 and 40 and the support extension 46. In this position, the cupping section 74 of the sheet 22 depends into the toilet bowl 18.

FIGS. 6a–6e are perspective views of the collection device 20 taken from the top (FIG. 6a), bottom (FIG. 6b), front (FIG. 6c), back (FIG. 6d), and side (FIG. 6e). These figures show a generally T-shaped device including the support or central extension 46 and a cross strip section 42 bisected by the support extension 46 to form first and second longitudinal cross extensions 38 and 40. The extensions 38, 40, and 46 meet generally at an intersection 30 and project outward. These extensions also have removable attachment apparatus 44 at respective ends distal from the intersection.

Also shown in FIGS. 6a–6e are left and right webbing sections 60 and 62 which are formed generally between the support extension 46 and the left and right longitudinal extensions 38 and 40, respectively. The left and right webbing sections 60 and 62 are generally bisected by left and right diagonal fold lines 24 and 26, respectively. The diagonal fold lines 24 and 26 are at approximately a 45° angle to both the support extension 46 and the left and right longitudinal extensions 38 and 40. Additional backward L-shaped and L-shaped cupping fold lines 32 and 34 are preferably formed on the left and right webbing sections 60 and 62, respectively. These cupping fold lines 32 and 34 cause the diagonal fold lines 24 and 26 to form a bottom of a cupping section 74 near the intersection 30 and to form sides of the cupping section 74 at respective ends of the diagonal fold lines 24 and 26 distal to the intersection 30.

FIG. 7 shows the approximate preferred dimensions of the collection device 20. The preferred embodiment has an approximate overall height 100 of 8.375 inches from the bottom edge of strip 42 to the top edge of extension 46. The overall height 100 is broken up into four sections: strip 42 has an approximate height 102 of 2.000 inches; the next section above has an approximate height 104 of 2.125 inches; the next section above has an approximate height 106 of 2.250 inches; and the top section has an approximate height 108 of 2.000 inches. The preferred embodiment has an approximate overall width 110 of 12.500 inches measured from the edges of extensions 38 and 40 which is preferably symmetrical around the center line 68. Accordingly, half the width 112 is approximately 6.250 inches measured from the center line 68 to the edge of either longitudinal extension 38 or 40. The approximate width 114 from the center line 68 to the end of the lower end of the diagonal fold line 26 is 1.994 inches. The approximate width 116 from the lower end of the diagonal fold line 26 to the edge of extension 38 is 4.256. The approximate width 118 of the support extension 46 is 2.000 inches. The approximate width 120 of the shoulder between extension 46 and the cupping section 74 is 1.000 inches. The approximate width 122 between the upper leg of fold line 32 and the upper end of the diagonal fold line 24 measured parallel to the bottom edge of the device 20 is 1.125 inches. The approximate height 122 between the upper end of the diagonal fold line 24 and the lower leg of fold line 32 and measured perpendicular to the bottom edge of the device 20 is 1.125 inches. The approximate distance 126 between the upper and lower legs of fold line 34 taken parallel to the preferred edge (which is preferably cut at an angle 128 of 45° to a line parallel to the center line 68) defined therebetween is 3.182 inches. The approximate distances 130 and 132 between the upper end of the diagonal fold line 26 and the upper and lower legs of fold line 34, respectively, taken parallel to the preferred edge defined therebetween are 1.591 inches. These dimensions are meant to be approximate and are not meant to limit the scope of the invention. Further, it is anticipated that the dimensions may be adapted to fit toilet bowls of various sizes either by adjusting the dimensions of the device 20 proportionately or by increasing the dimensions of various components such as elongating the extensions 38, 40, and 46.

The shoulder corners 134 are preferably cut at a radius of 0.200 degrees which adds strength to the device 20 since this type of cut is less likely to tear than a corner cut at a right angle.

Additional fold lines may also be added. For example, a fold line which corresponds to the section of the center line 68 located on the strip 42 may be added to increase the rigidity of the cupping section 74.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed:

1. A stool sample collection apparatus comprising:
   (a) a sheet having first and second diagonal fold lines, the first and second diagonal fold lines intersecting in a bottom half of the sheet;
   (b) a longitudinal fold line generally intersecting the intersection of the first and second diagonal fold lines;
   (c) left and right longitudinal extensions defined by and on opposite ends of a strip of the sheet between an edge of the sheet and the longitudinal fold line, the left and right longitudinal extensions having attachment apparatus;
   (d) a support extension formed from the sheet, the support extension midway and perpendicular to the left and right longitudinal extensions, the support extension having attachment apparatus; and
   (e) a cupping section in the sheet formed by the first and second diagonal fold lines and the longitudinal fold line, the cupping section generally between the left and right longitudinal extensions and the support extension;
   wherein the attachment apparatus on the left and right longitudinal extensions and the support extension are attachable to a rim of a toilet bowl so that the cupping section of the sheet depends into the toilet bowl.

2. The apparatus of claim 1 further comprising additional fold lines on the cupping section of the sheet to add extra rigidity to the cupping section.

3. The apparatus of claim 1 wherein the attachment apparatus is removable adhesive.

4. The apparatus of claim 1 wherein the attachment apparatus is covered by a removable protective covering which is removed prior to the attachment apparatus being attached to the rim of the toilet bowl.

5. The apparatus of claim 1 wherein the left and right longitudinal extensions and the support extension have folds to permit the attachment apparatus to attach to its respective extension for protection, the attachment apparatus being removed from its respective extension and the fold being removed from the extension prior to the attachment apparatus being attached to the rim of the toilet bowl.

6. A foldable stool sample collection device comprising:
   (a) a sheet of foldable material;
   (b) at least three extensions formed from the sheet, the extensions meeting generally at an intersection;
   (c) an adhesive tab located at respective ends of the extensions distal from the intersection; and
   (d) a cupping section formed from the sheet and generally at the intersection, the cupping section forming at least two webbing sections, a first webbing section generally between a first extension and a second extension and a second webbing section generally between the second extension and a third extension, the webbing sections having fold lines to add shape and rigidity to the cupping section;
   wherein the adhesive tab is attachable to a rim of a toilet bowl so that the cupping section depends into the toilet bowl.

7. The device of claim 6 wherein the foldable material is paper.

8. The device of claim 6 wherein the foldable material is biodegradable.

9. The device of claim 6 wherein said foldable material folds along said fold lines.

10. The device of claim 6 wherein the sheet is generally T-shaped to include a central extension and a cross extension bisected by the central extension, the first webbing section formed between a first side of the cross extension and the central extension and the second webbing section formed between a second side of the cross extension and the central extension, said fold lines comprising:
    (a) a first diagonal fold line on said first webbing section at approximately a 45° angle to both the first side of the cross extension and the central extension; and
    (b) a second diagonal fold line on said second webbing section at approximately a 45° angle to both the second side of the cross extension and the central extension.

11. The device of claim 10, further comprising fold lines on said first and second webbing sections which cause said first and second diagonal fold lines to form a bottom of the cupping section near the intersection and to form sides of the cupping section at respective ends of the first and second diagonal fold lines distal to the intersection.

12. A disposable stool sample collector for use in association with a toilet bowl having a rim, the collector comprising:
    (a) a generally T-shaped disposable sheet including a central extension and a cross section bisected by the central extension to form first and second cross extensions, said central, first, and second extensions meeting at an intersection and projecting outward, said extensions having removable attachment apparatus at respective ends distal from the intersection;
    (b) a first webbing section formed between the first cross extension and the central extension, the first webbing section generally bisected by a first diagonal fold line at approximately a 45° angle to both the first cross extension and the central extension;

(c) a second webbing section formed between the second cross extension and the central extension, the second webbing section generally bisected by a second diagonal fold line at approximately a 45° angle to both the second cross extension and the central extension; and (d) first and second cupping fold lines formed on said first and second webbing sections which cause said first and second diagonal fold lines to form a bottom of a cupping section near the intersection and to form sides of the cupping section at respective ends of the first and second diagonal fold lines distal to the intersection;

wherein the removable attachment apparatus is attached to the rim so that the cupping section depends into the toilet bowl.

13. The collector of claim 12 wherein the attachment apparatus is removable adhesive.

14. The collector of claim 12 wherein the attachment apparatus is covered by a removable protective covering which is removed prior to the attachment apparatus being attached to the rim of the toilet bowl.

15. The collector of claim 12 wherein the disposable sheet is paper.

16. The collector of claim 12 wherein the disposable sheet is biodegradable.

* * * * *